US010130253B2

(12) United States Patent
Roorda et al.

(10) Patent No.: US 10,130,253 B2
(45) Date of Patent: Nov. 20, 2018

(54) SCANNING LASER OPHTHALMOSCOPE FOR REAL-TIME EYE TRACKING AND METHOD OF OPERATING SAME

(71) Applicant: THE REGENTS OF THE UNIVERSITY OF CALIFORNIA, Oakland, CA (US)

(72) Inventors: Austin J. Roorda, El Cerrito, CA (US); Christy K. Sheehy, Berkeley, CA (US); Pavan Tiruveedhula, Fremont, CA (US); William Tuten, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/524,822

(22) PCT Filed: Nov. 6, 2015

(86) PCT No.: PCT/US2015/059479
§ 371 (c)(1),
(2) Date: May 5, 2017

(87) PCT Pub. No.: WO2016/073859
PCT Pub. Date: May 12, 2016

(65) Prior Publication Data
US 2017/0340202 A1 Nov. 30, 2017

Related U.S. Application Data
(60) Provisional application No. 62/077,022, filed on Nov. 7, 2014.

(51) Int. Cl.
A61B 3/12 (2006.01)
A61B 3/10 (2006.01)
A61B 3/113 (2006.01)

(52) U.S. Cl.
CPC ............ *A61B 3/1025* (2013.01); *A61B 3/102* (2013.01); *A61B 3/113* (2013.01); *A61B 3/12* (2013.01)

(58) Field of Classification Search
CPC ......... A61B 3/102; A61B 3/12; A61B 3/1025; A61B 3/113
(Continued)

(56) References Cited

U.S. PATENT DOCUMENTS 5,673,097 A 9/1997 Heacock
6,890,076 B2 5/2005 Roorda
(Continued)

OTHER PUBLICATIONS

International Search Report (PCT/ISA/210) dated Feb. 29, 2016, by the Korean Intellectual Patent Office as the International Searching Authority for International Application No. PCT/US2015/059479.
(Continued)

*Primary Examiner* — Hung Dang
(74) *Attorney, Agent, or Firm* — Buchanan Ingersoll & Rooney PC

(57) ABSTRACT

A scanning laser ophthalmoscope and a method of operating a scanning laser ophthalmoscope are disclosed. The scanning laser ophthalmoscope includes a light source, a reflective optical system, an x- and y-coordinate scanner, and a refractive lens. The reflective optical system is configured to direct light emitted from the light source through the refractive lens to a user's eye, and to direct light reflected from the user's eye through the refractive lens to the x- and y-coordinate scanner.

14 Claims, 2 Drawing Sheets

(58) Field of Classification Search
USPC .................................. 351/210, 246, 206, 205
See application file for complete search history.

(56) References Cited

U.S. PATENT DOCUMENTS

| | | |
|---|---|---|
| 2006/0114411 A1 | 6/2006 | Wei et al. |
| 2009/0141240 A1 | 6/2009 | Weitz et al. |
| 2013/0188140 A1* | 7/2013 | Bagherinia ............ A61B 3/102 351/206 |
| 2013/0211514 A1 | 8/2013 | Peyman |
| 2014/0226130 A1 | 8/2014 | Everett et al. |

OTHER PUBLICATIONS

Written Opinion (PCT/ISA/237) dated Feb. 29, 2016, by the Korean Intellectual Patent Office as the International Searching Authority for International Application No. PCT/US2015/059479.
Rucci, M. et al., "Miniature eye movements enhance fine spatial detail", Nature, vol. 447, p. 851-855, Jun. 14, 2007.
Riggs, L. A. et al., "Accuracy of retinal image stabilization achieved with a plane mirror on a tightly fitting contact lens", Visions Res., vol. 8, pp. 159-169,1968.
Guizar-Sicairos, M. et al., "Efficient subpixel image registration algorithms", Optics Letters, vol. 33, No. 2, pp. 156-168, Jan. 15, 2008.
Martinez-Conde, S. et al., "The role of fixational eye movements in visual perception", Nature Reviews, Neuroscience, vol. 5, pp. 229-240, Mar. 2004.
Arathorn, D. W. et al., "Retinally stabilized cone-targeted stimulus delivery", Optics Express, vol. 15, No. 21, pp. 13731-13744, Oct. 17, 2007.
Garcia-Martin, Phd, E. et al., "Optical coherence tomography in retinitis pigmentosa, Reproducibility and Capacity to Detect Macular and Retinal Nerve Fiber Layer Thickness Alterations", Retina, The Journal of Retinal and Vitreous Diseases, vol. 32, No. 8, pp. 1581-1591, 2012.
Martinez-Conde, S. et al., "Fixational eye movements in normal and pathological vision", Progress in Brain Research, Elsevier B.V., vol. 154, Chapter 8, pp. 151-176, 2006.
Rolfs, M., "Microsaccades: Small steps on a long way", Vision Research 49, Elsevier, pp. 2415-2441, 2009.
Merino, D. et al., "Observation of cone and rod photoreceptors in normal subjects and patients using a new generation adaptive optics scanning laser ophthalmoscope", Biomedical Optics Express, vol. 2, No. 8, pp. 2189-2201, Aug. 1, 2011.
Stevenson, S. B. et al., "Correcting for miniature eye movements in high resolution scanning laser ophthalmoscopy", Proc. of SPIE, vol. 5688, pp. 145-151, 2005.
Dubra, A. et al., "Reflective afocal broadband adaptive optics scanning ophthalmoscope", Biomedical Optics Express, vol. 2, No. 6, pp. 1757-1768, Jun. 1, 2011.

Martinez-Conde, S. et al., "Microsaccades: a neurophysiological analysis", Trends in Neurosciences, vol. 32, No. 9, pp. 463-475, 2009.
Hammer, D. X. et al., "Adaptive optics scanning laser ophthalmoscope for stabilized retinal imaging", Optics Express, vol. 14, No. 8, pp. 3354-3367, Apr. 17, 2006.
Santini, F. et al., "EyeRIS: A general-purpose system for eye-movement-contingent display control", Behavior Research Methods, EYERIS, vol. 39, No. 3, pp. 350-364, 2007.
Crane, H. D. et al., "Generation-V dual-Purkinje-image eyetracker", Applied Optics, vol. 24, No. 4, pp. 527-537, Feb. 15, 1985.
Cornsweet, T. N. et al., "Accurate two-dimensional eye tracker using first and fourth Purkinje images", Journal of the Optical Society of America, vol. 63, No. 8, pp. 921-928, Aug. 1973.
Riggs, L.A et al., "Motions of the Retinal Image during Fixation", Journal of the Optical Society of America, vol. 44, No. 4, pp. 315-321, Apr. 1954.
Stevenson, S. B. et al., "Eye Tracking with the Adaptive Optics Scanning Laser Ophthalmoscope", pp. 195-197, Mar. 2010.
Mulligan, J. B., "Recovery of motion parameters from distortions in scanned images", Proceedings of the Image Registration Workshop, NASA Goddard Space Flight Center, Greenbelt, MD, NASA Publication #CP-1998-206853, pp. 281-292, Nov. 20-21, 1997.
Poonja, S. et al., "Dynamic Visual Stimulus Presentation in an Adaptive Optics Scanning Laser Ophthalmoscope", Journal of Refractive Surgery, vol. 21, pp. S575-S580, Sep./Oct. 2005.
Gömez-Vieyra, A. et al., "First-order design of off-axis reflective ophthalmic adaptive optics systems using afocal telescopes", Optics Express, vol. 17, No. 21, pp. 18906-18919, Oct. 12, 2009.
Yang, Q. et al., "Design of an integrated hardware interface for AOSLO image capture and cone-targeted stimulus delivery", Optics Express, vol. 18, No. 17, pp. 17841-17858, Aug. 16, 2010.
Vogel, C. R. et al., "Retinal motion estimation in adaptive optics scanning laser ophthalmoscopy", Optics Express, vol. 14, No. 2, pp. 487-497, Jan. 23, 2006.
Sincich, L. C. et al., "Resolving single cone inputs to visual receptive fields", Nature Neuroscience, vol. 12, No. 8, pp. 967-968, Aug. 2009.
Sadda, S. R. et al., "Impact of Scanning Density on Measurements from Spectral Domain Optical Coherence Tomography", Investigative Ophthalmology & Visual Science, vol. 51, No. 2, pp. 1071-1078, Feb. 2010.
Sheehy, C. K. et al., "High-speed, image-based eye tracking with a scanning laser ophthalmoscope", Biomedical Optics Express, vol. 3, No. 10, pp. 2611-2622, Pub. Sep. 19, 2012, Oct. 1, 2012.
Harmening, W. M., et al., "Measurement and Correction of transverse chromatic offsets for multi-wavelength retinal microscopy in the Living eye", Biomedical Optics Express, vol. 3, No. 9, pp. 2066-2077, Sep. 1, 2012.
Poloschek, C. M. et al., "The fine structure of multifocal ERG topographies", Journal of Vision, vol. 2, pp. 577-587, 2002.

* cited by examiner

SCANNING LASER OPHTHALMOSCOPE FOR REAL-TIME EYE TRACKING AND METHOD OF OPERATING SAME

CROSS-REFERENCE TO RELATED APPLICATION

This application is a non-provisional application claiming the benefits of U.S. Provisional Patent Application Ser. No. 62/077,022 filed on Nov. 7, 2014, the content of which is hereby incorporated by reference.

FIELD

The present disclosure relates to a scanning laser ophthalmoscope for real-time eye tracking and a method for operating a scanning laser ophthalmoscope for real-time eye tracking.

BACKGROUND INFORMATION

Conventional scanning laser ophthalmoscopes provide structural imaging and real-time eye tracking and targeted stimulus delivery. For examples, Sheehy et al., High-speed, image-based eye tracking with a scanning laser ophthalmoscope, Biomedical Optics Express, Sep. 19, 2012, describes a confocal scanning laser ophthalmoscope. This scanning laser ophthalmoscope includes a light source, a reflective mirror assembly, and an x- and y-coordinate scanner. In one optical design described in this publication, light exiting a super luminescent diode (SLD) is coupled into an acousto-optic modulator (AOM) before entering the system. The light is collimated and sent through a basic 4f series of lenses onto an adjustable aperture (A1). Light travels through three mirror-based telescope assemblies (f=250 mm) to the human eye. Light is then reflected off the retina and sent back through the system into the light detection arm. Another series of lenses in a 4f configuration relays the light to be collected by a photomultiplier tube (PMT). A 50 μm pinhole (1.95 Airy disc diameters for a 4 mm pupil) is placed at the retinal conjugate plane prior to the PMT for confocality. The intensity (I) of the signal is sent to a personal computer (PC) for readout. This system, like other similar systems in the conventional art, is however limited to a 5-degree field of view. Moreover, this system is not suited for certain applications requiring the tracking of large eye movements or rapid eye movements.

Furthermore, the scanning laser ophthalmoscope described in Sheehy et al., High-speed, image-based eye tracking with a scanning laser ophthalmoscope, Biomedical Optics Express, Sep. 19, 2012 tracks eye motion in the following manner. A reference frame is selected (usually the first frame to occur in a scanning laser ophthalmoscope movie). Each subsequent frame is broken up into a set number of strips that are parallel to the fast scanner. Each strip within a subsequent frame is then linearly cross-correlated with the reference frame to create a stabilized version of that subsequent frame. The (x,y) displacements required to stabilize this frame with respect to the reference frame are used to measure the relative cardinal motion of the eye. Every subsequent frame can then be redrawn to be aligned with the reference frame. This occurs in real-time so that the operator can see both the subject's actual retinal motion and the stabilized version of the retina side by side on the software interface. Using the real-time eye trace generated from the (x,y) displacements of each frame as described above, the timing of the stimulus delivery can be controlled to guide its placement to any targeted location on the retina.

One of the problems with choosing a single reference frame for eye tracking in this manner is that, when the eye moves perpendicular to the orientation of the strips that are used for eye tracking in the image, the new regions of the retina that are imaged may no longer overlap with the reference frame. This can lead to a non-uniformly sampled eye motion trace. Frame rates and image quality can also be limited when imaging or testing.

Furthermore, microperimeters are devices that are capable of simultaneous retinal imaging and subjective visual function testing. Microperimetry has clinical utility because it can provide functional correlates to the structure observed in retinal images obtained from patients with retinal disease. In some cases, the fidelity of this link between structure and function depends on two factors: (1) image resolution, which determines the structures that can and cannot be visualized in the retinal image; and (2) the precision and accuracy of visual stimulation. Because the eye is always in motion, many conventional microperimeters use image-based retinal tracking to deliver visual stimuli more accurately. As a result, (2) can be heavily dependent on (1), among other factors. Current microperimeters typically employ images captured over large fields-of-view (~30 degrees) and with relatively low lateral resolution to track eye motion at the rate of image acquisition (20-30 Hz). This is explained in Midena, E. Perimetry and the fundus: an introduction to microperimetry. (SLACK Inc., 2007), which is hereby incorporated by reference for its description of microperimetry. In addition, Harmening, W. M., Tiruveedhula, P., Roorda, A. & Sincich, L. C. Measurement and correction of transverse chromatic offsets for multi-wavelength retinal microscopy in the living eye. Biomedical optics express 3, 2066-2077, doi:10.1364/BOE.3.002066 (2012) is hereby incorporated by reference for its description of chromatic aberration. Current systems do not offer much flexibility in terms of stimulus wavelength composition and are unable to measure and account for imprecision introduced by the chromatic aberration of the eye.

In addition, electroretinography (ERG) is a technique for measuring retinal function objectively. ERG involves placing an electrode on or near the front of the eye to detect the small electrical changes in the retina that are triggered by the presentation of visual stimuli on a computer monitor. Multifocal ERG (mfERG) is a variant of ERG that yields spatially-resolved measures of outer retinal function. Conventional mfERG devices have a spatial resolution much coarser than the scale of many disease-induced retinal abnormalities, such as retinal drusen, and are thus unable to fully characterize their functional implications. The spatial resolution of mfERG is primarily limited by low signal-to-noise ratios. One way to improve signal-to-noise ratios is to simply collect more data. However, protracted recording sessions with finer-grained stimuli have conventionally only yielded sensible data in cases where fixation was exceptionally stable, often in young and healthy subjects. This is due to the fact that eye movements during the recording session can shift the stimulus to different and unwanted parts of the retina from one moment to the next, with the resultant mfERG recording comprising activity measured from a broader swath of retina than originally intended. This is explained in Sutter, E. E. & Tran, D. The field topography of ERG components in man—I. The photopic luminance response. Vision Res 32, 433-446 (1992), and Poloschek, C. M. & Sutter, E. E. The fine structure of multifocal ERG topographies. J Vis 2, 577-587, doi:10.1167/2.8.5 (2002), which are both hereby incorporated by reference for their description of mfERG.

SUMMARY

A scanning laser ophthalmoscope is disclosed. The scanning laser ophthalmoscope comprises a light source, a reflective optical system, an x- and y-coordinate scanner, and a refractive lens. The reflective optical system is configured to direct light emitted from the light source through the refractive lens to a user's eye, and to direct light reflected from the user's eye through the refractive lens to the x- and y-coordinate scanner.

A method of operating a scanning laser ophthalmoscope is disclosed. The scanning laser ophthalmoscope comprises a reflective optical system, an x- and y-coordinate scanner, and a refractive lens, the reflective optical system configured to direct light emitted from the light source through the refractive lens to a user's eye, and to direct light reflected from the user's eye through the refractive lens to the x- and y-coordinate The method comprises obtaining a first reference frame using the scanning laser ophthalmoscope, the first reference frame having a first field of view, the first reference frame including a first number of scanned lines and a first line separation between the scanned lines, obtaining a second frame using the scanning laser ophthalmoscope, the second frame including a second number of scanned lines smaller than the first number of scanned lines and a second line separation between the scanned lines equal to the first line separation, dividing the second frame into a plurality of strips, determining a second linearly stabilized frame by linearly cross-correlating each of the plurality of strips with the first reference frame, and determining a plurality of linear displacement values, each of the plurality of linear displacement values associated with a positional difference between one of the plurality of strips and the first reference frame.

BRIEF DESCRIPTION OF THE DRAWINGS

Other features and advantages disclosed herein will become more apparent from the following detailed description of exemplary embodiments when read in conjunction with the attached drawings, wherein.

DETAILED DESCRIPTION

Sheehy et al., High-speed, image-based eye tracking with a scanning laser ophthalmoscope, Biomedical Optics Express, Sep. 19, 2012 is hereby incorporated by reference for its description of scanning laser ophthalmoscopes and methods of operating scanning laser ophthalmoscopes.

U.S. Pat. No. 6,890,076 B2 to Austin Roorda is hereby incorporated by reference for its description of scanning laser ophthalmoscopes and methods of operating scanning laser ophthalmoscopes.

Figure 1:
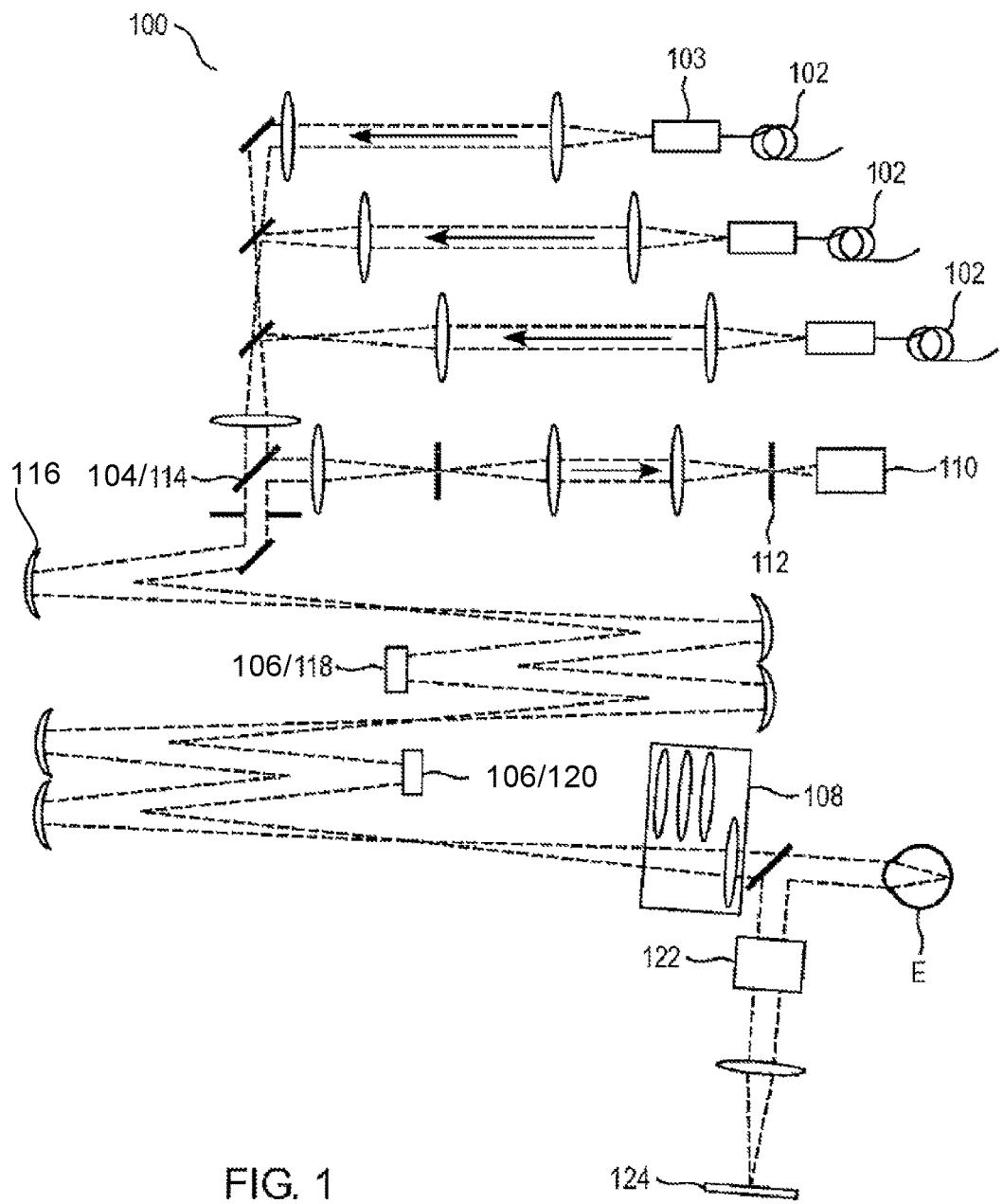
FIG. 1 shows an exemplary embodiment of a scanning laser ophthalmoscope.

FIG. 1 shows exemplary embodiments of a scanning laser ophthalmoscope 100. The scanning laser ophthalmoscope 100 includes a light source 102, a reflective optical system 104, an x- and y-coordinate scanner 106, and a refractive lens 108. The reflective optical system 104 is configured to direct light emitted from the light source 102 through the refractive lens 108 to a user's eye E, and to direct light reflected from the user's eye E through the refractive lens 108 to the x- and y-coordinate scanner 106. Although lenses can create glare where mirror would instead produce a cleaner image, using a refractive lens 108 instead of a mirror to direct light toward a user's eye E can provide a larger field of view, and can be better suited for certain applications requiring the tracking of large eye movements or rapid eye movements. Moreover, using a refractive lens 108 can render the optical path more easily accessible and easier to join with other systems, such as, but not limited to, optical coherence tomography systems or adaptive optics scanning laser ophthalmoscopes, and can also facilitate preparing and setting up for patient imaging.

In an exemplary embodiment, a light source 102 is one of multiple light sources emitting light of different wavelengths. For example, light sources 102 can include two visible light sources of different wavelengths, and an infrared light source. Suitable visible light wavelengths include, but are not limited to, 532 nm light and 600 nm. Suitable infrared light wavelengths include, but are not limited to 680 nm, 730 nm, 740 nm, and 840 nm. A light source can be manufactured to emit light of a particular wavelength, or can be adjustable. For example, a light source can be a white light source in combination with one or more filters that only transmit light of a specific wavelength. In an exemplary embodiment, visible light is used for microperimetry, and infrared light is used for imaging. In an exemplary embodiment, a light source 102 includes a superluminescent diode. A light source 102 can include or be coupled to one or more high speed acousto-optic light modulators 103.

In an exemplary embodiment, the scanning laser ophthalmoscope 100 includes a light-sensitive detector 110, such as, but not limited to a charge-coupled device (CCD) detector, to measure the intensity of light travelling through the ophthalmoscope 100. For example, the light-sensitive detector 110 includes a photomultiplier tube light detector that collects light from a confocal pinhole 112, as illustrated in FIG. 1.

In an exemplary embodiment, the reflective optical system 104 includes a beam splitter 114 that direct a beam toward the light-sensitive detector 110 and another beam of light toward a curved relay mirror 116. The curved relay mirror is configured to direct light toward the x- and y-coordinate scanner 106.

In an exemplary embodiment, the x- and y-coordinate scanner 106 is a single mirror.

In an exemplary embodiment, the x- and y-coordinate scanner 106 includes a fast-scan mirror 118 and a slow-scan mirror 120. In an exemplary embodiment, the fast-scan mirror 118 is configured to operate at a frequency of 15.75 kHz and includes an aperture of 4 mm. In an exemplary embodiment, the slow-scan mirror 120 is configured to operate at a frequency of 30 Hz.

In an exemplary embodiment, the scanning laser ophthalmoscope includes an optical stabilization module 122 and an external display device 124. The optical stabilization module 122 can include hardware components, or hardware components combined with software components. In an exemplary embodiment as shown in FIG. 1, a beamsplitter is placed between the refractive lens 108 and the eye E so that the scanning beam and the external display 124 are displayed simultaneously onto the retina of the eye E. The external display 124 is viewed through an optical stabilization module 122. The optical stabilization module 122 stabilizes the eye's view of the external display device 124.

The external display device can include a computer screen or any other display with a fast flicker rate.

In an exemplary embodiment, the software component of the optical stabilization module 122 is configured to stabilize and track eye motion in real-time and deliver stimulus at the same time in multiple wavelength channels.

In an exemplary embodiment, the refractive lens 108 is replaced by a different refractive lens 108 positioned so that the emergent scanning beam is collimated. When placed in this manner, refractive lenses with shorter focal lengths will give rise to larger fields of view.

In an exemplary embodiment, the refractive lens 108 is a first refractive lens possessing a first focal length and is replaceable with a second refractive lens possessing a second focal length different from the first focal length. In an exemplary embodiment, the refractive lens 108 possesses an adjustable focal length. For example, the refractive lens 108 can include a flexible lens. In an exemplary embodiment, a lens carousel can be used to provide modular swapping of lenses with different focal lengths. Alternatively, any movable or adjustable lens system can be used, so long as it is configured to adjust the field of view.

Figure 2:
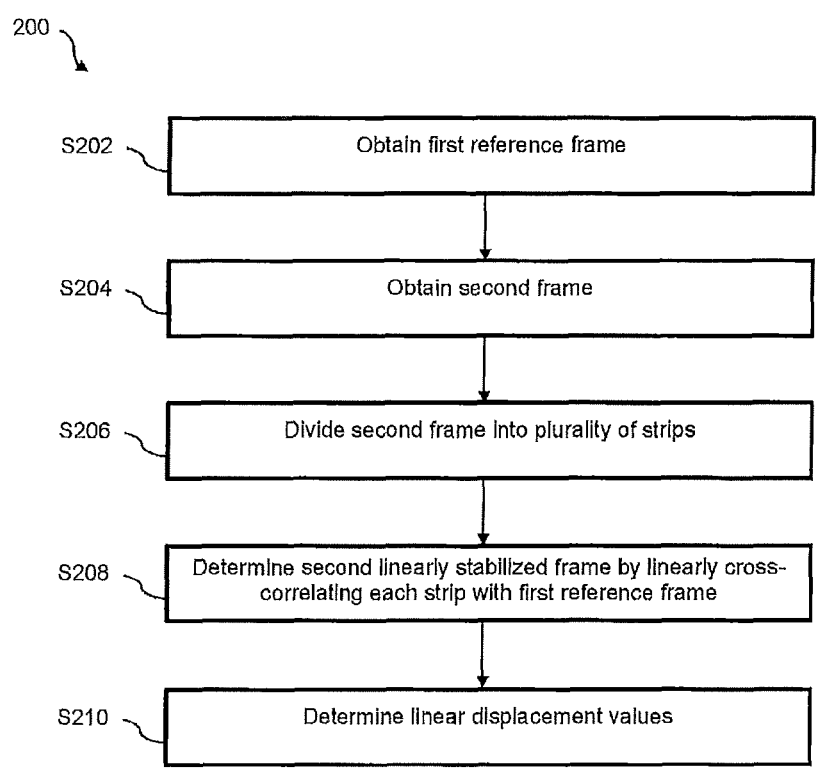
FIG. 2 shows a block diagram of an exemplary method of operating a scanning laser ophthalmoscope.

FIG. 2 shows a block diagram of an exemplary method 200 of operating a scanning laser ophthalmoscope. The scanning laser ophthalmoscope includes a reflective optical system, an x- and y-coordinate scanner, and a refractive lens, the reflective optical system configured to direct light emitted from the light source through the refractive lens to a user's eye, and to direct light reflected from the user's eye through the refractive lens to the x- and y-coordinate scanner. The method 200 includes step S202 of obtaining a first reference frame using the scanning laser ophthalmoscope, the first reference frame having a first field of view, the first reference frame including a first number of scanned lines and a first line separation between the scanned lines, step S204 of obtaining a second frame using the scanning laser ophthalmoscope, the second frame including a second number of scanned lines smaller than the first number of scanned lines and a second line separation between the scanned lines equal to the first line separation, step S206 of dividing the second frame into a plurality of strips, step S208 of determining a second linearly stabilized frame by linearly cross-correlating each of the plurality of strips with the first reference frame, and step S210 of determining a plurality of linear displacement values, each of the plurality of linear displacement values associated with a positional difference between one of the plurality of strips and the first reference frame. This method allows for the detection of cardinal movements of a user's eye.

In an exemplary method 200 of operating a scanning laser ophthalmoscope, an advantage is that images captured using smaller dimension frames subsequent to the reference frame in some cases is able to capture retinal images over a larger range of motion without losing overlap with the reference frame in a direction perpendicular to the orientation of the strips used for tracking. Thus the tracking scanning laser ophthalmoscope operated in this manner is in some cases able to track retinal motion more continuously over a larger range. The range of retinal motion in a direction perpendicular to the orientation of the strips used for tracking, over which the tracking scanning laser ophthalmoscope is able to record eye motion continuously, is in some cases equal to the reduction in field size. The use of a small field of view frame subsequent to the reference frame in some cases also increases the frame rate of image capture in a manner that is inversely proportional to the reduced field size. In some cases, if the scanning beam is used for light stimulus delivery to the retina, then the rate of light delivery will also be increased.

In an exemplary method 200 of operating a scanning laser ophthalmoscope, at least two of the plurality of strips partially overlap one another. In some embodiments, obtaining a set of overlapping strips leads to a more uniformly sampled eye motion trace.

In an exemplary method 200 of operating a scanning laser ophthalmoscope, at least two of the plurality of strips are adjacent to one another.

An exemplary method of operating a scanning laser ophthalmoscope further comprises a step of dividing the second frame into a first portion and a second portion, a step of determining a second rotationally stabilized frame by rotationally cross-correlating each of the first and second portions with the first reference frame, and a step of determining a rotational displacement value associated with the rotational cross-correlation of the first and second portions with the first reference frame. This method allows for the detection of torsional movements of a user's eye about an axis running from the eye to the detector, which in some cases coincides with the visual axis of the eye or with the optical axis of the eye In an exemplary method, the first and second portions are equal in size. Alternatively, the first and second portions are not equal in size.

An exemplary method 200 of operating a scanning laser ophthalmoscope further comprises the use of adaptive optics to reduce blur caused by optical imperfections in the eye.

An exemplary method 200 of operating a scanning laser ophthalmoscope further comprises performing a microperimetry procedure. Improvements in the precision and accuracy with which microperimetry is conducted can be achieved with improved retinal image resolution and higher-speed eye tracking, all while maintaining a field-of-view that is large enough to remain robust to larger eye motions associated with retinal disease. A system capable of measuring and correcting for chromatic aberration can further improve the accuracy and precision of visual stimulation for microperimetry. An exemplary embodiment of the scanning laser ophthalmoscope 100 improves on the current state-of-the-art of microperimetry by providing enhanced image resolution, high-speed and robust eye tracking, and the capacity for multi-channel imaging required to compensate for the effects of chromatic aberration.

An exemplary method 200 of operating a scanning laser ophthalmoscope further comprises performing an electroretinography procedure. Active eye tracking with an exemplary embodiment of the scanning laser ophthalmoscope 100 improves the confidence with which mfERG traces can be attributed to precise locations on the retina by keeping the mfERG stimulus locked onto the moving retina, and thus allows for the longer recording sessions necessary for finer-scale mfERG recording. An exemplary method 200 of operating a scanning laser ophthalmoscope produces a retinally contingent mfERG stimulus by: (1) presenting the stimulus pattern via direct high-speed modulation of the visible light channels within the scanning laser ophthalmoscope 100 raster; or (2) feeding eye tracking signals into an active optical stabilization module 122 situated between an external display device 124 and the eye E. In either case, incorporating active eye tracking offered by scanning laser ophthalmoscope imaging improves the current state-of-the-art for mfERG recording.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A scanning laser ophthalmoscope, comprising:
a light source;
a reflective optical system;
an x- and y-coordinate scanner; and
a refractive lens,
wherein the reflective optical system is configured to direct light emitted from the light source through the refractive lens to a user's eye, and to direct light reflected from the user's eye through the refractive lens to the x- and y-coordinate scanner.

2. The scanning laser ophthalmoscope of claim 1, wherein the light source is a first light source configured to emit visible light, and the scanning laser ophthalmoscope comprises a second light source configured to emit infrared light.

3. The scanning laser ophthalmoscope of claim 1, wherein the refractive lens possesses an adjustable focal length.

4. The scanning laser ophthalmoscope of claim 1, wherein the x- and y-coordinate scanner is a single mirror.

5. The scanning laser ophthalmoscope of claim 1, wherein the refractive lens is movable to vary a field of view of the scanning laser ophthalmoscope.

6. The scanning laser ophthalmoscope of claim 1, wherein the refractive lens is a first refractive lens possessing a first focal length and is replaceable with a second refractive lens possessing a second focal length different from the first focal length.

7. The scanning laser ophthalmoscope of claim 1, further comprising a light-sensitive detector configured to measure the intensity of light travelling through the scanning laser ophthalmoscope.

8. The scanning laser ophthalmoscope of claim 1, further comprising an optical stabilization module configured to stabilize an image contained in light emitted from the refractive lens.

9. The scanning laser ophthalmoscope of claim 1, further comprising an external display device configured to receive light from the optical stabilization module.

10. A method of operating a scanning laser ophthalmoscope, the scanning laser ophthalmoscope comprising a reflective optical system, an x- and y-coordinate scanner, and a refractive lens, the reflective optical system configured to direct light emitted from the light source through the refractive lens to a user's eye, and to direct light reflected from the user's eye through the refractive lens to the x- and y-coordinate scanner, the method comprising:
obtaining a first reference frame using the scanning laser ophthalmoscope, the first reference frame having a first field of view, the first reference frame including a first number of scanned lines and a first line separation between the scanned lines;
obtaining a second frame using the scanning laser ophthalmoscope, the second frame including a second number of scanned lines smaller than the first number of scanned lines and a second line separation between the scanned lines equal to the first line separation;
dividing the second frame into a plurality of strips;
determining a second linearly stabilized frame by linearly cross-correlating each of the plurality of strips with the first reference frame; and
determining a plurality of linear displacement values, each of the plurality of linear displacement values associated with a positional difference between one of the plurality of strips and the first reference frame.

11. The method of operating a scanning laser ophthalmoscope of claim 10, wherein at least two of the plurality of strips partially overlap one another.

12. The method of operating a scanning laser ophthalmoscope of claim 10, wherein at least two of the plurality of strips are adjacent to one another.

13. The method of operating a scanning laser ophthalmoscope of claim 10, comprising performing a microperimetry procedure.

14. The method of operating a scanning laser ophthalmoscope of claim 10, comprising performing an electroretinography procedure.

* * * * *

UNITED STATES PATENT AND TRADEMARK OFFICE
CERTIFICATE OF CORRECTION

PATENT NO. : 10,130,253 B2
APPLICATION NO. : 15/524822
DATED : November 20, 2018
INVENTOR(S) : Austin J. Roorda et al.

It is certified that error appears in the above-identified patent and that said Letters Patent is hereby corrected as shown below:

In the Specification

Line 12 the following statement is inserted as the second paragraph, after the paragraph under "CROSS-REFERENCE TO RELATED APPLICATION" and before "FIELD":
--This invention was made with government support under Grant Numbers EY014375, EY022412 and EY023591 awarded by the National Institutes of Health. The government has certain rights in the invention.--

Signed and Sealed this
Fifth Day of March, 2019

Andrei Iancu
*Director of the United States Patent and Trademark Office*